United States Patent [19]

Orlando et al.

[11] 4,037,732
[45] July 26, 1977

[54] POSITIONING APPARATUS

[75] Inventors: Anthony William Orlando, Highland; Frederick Arthur Schultz, Poughkeepsie, both of N.Y.

[73] Assignee: International Business Machines Corporation, Armonk, N.Y.

[21] Appl. No.: 646,312

[22] Filed: Jan. 2, 1976

[51] Int. Cl.² ............................................. B65G 47/90
[52] U.S. Cl. ................................................. 214/1 BB
[58] Field of Search ................. 214/1 BB, 1 BT, 1 B, 214/1 BS

[56] References Cited

U.S. PATENT DOCUMENTS

| 3,233,751 | 2/1966 | Bannon | 214/1 BB |
| 3,902,606 | 9/1975 | Ronbeck | 214/1 BV |

FOREIGN PATENT DOCUMENTS

| 343,274 | 1/1960 | Switzerland | 214/1 BB |
| 262,600 | 1/1970 | U.S.S.R. | 214/1 BB |

Primary Examiner—Frank E. Werner
Attorney, Agent, or Firm—Robert Lieber

[57] ABSTRACT

Apparatus for reciprocatively positioning an article or work object (e.g. an inspection sample or test probe) in precise relation to two separated work stations. The article to be positioned is held in a first carrier having a cam follower attachment. The first carrier is supported shiftably on a second carrier. The second carrier can be reciprocated perpendicular to the plane of the work stations. The cam follower of the first carrier is captured movably in a cam track groove of a stationary plate having two cam track grooves associated with respective said stations. A two-position rotatable cam forms a linking channel between the two tracks. Upon completion of a work operation at one of the stations the second carrier is reciprocated. This moves the cam follower of the first carrier up along one track and one associated surface of the cam to a reversing point above and beyond that surface, and then down along another surface of the cam into the other track; thereby transferring the work object to the other work station. The follower movement along said another surface rotates the cam so that on a next reciprocation of the second carrier the cam follower rides up said another surface to said reversing point and down the one surface into the one track; reversely tipping the cam to its original position as it rides along said one surface.

5 Claims, 6 Drawing Figures

POSITIONING APPARATUS

BACKGROUND OF THE INVENTION

Cross-Reference to Related Patent Applications

U.S. Pat. No. 3,978,992, entitled "Positioning Apparatus," by A. P. Mulzet et al, granted Sept. 7, 1976 and assigned to the assignee of this application.

1. Field of the Invention

Apparatus for precisely positioning an object or objects relative to plural work station positions.

2. Description of the Prior Art

As indicated in the above cross-referenced patent application by Mulzet et al there are many applications for positioning objects — e.g. probes, drills, integrated circuit chips, test specimens, etc. — precisely relative to plural discretely spaced work station positions. Known apparatus for this purpose employs an elaborate (and expensive) sprocket chain drive. The present invention provides conveying apparatus having more precise and reliable operation and featuring a simpler and less expensive belt and pulley drive cooperative with two movable carriers and a cam system having relatively simple construction.

SUMMARY OF THE INVENTION

An object of this invention is to provide improved apparatus for positioning articles relative to plural discrete work stations; characterized by ruggedness, reliability, simplicity, relatively few moving parts, preciseness of positioning operation, and adaptiveness to utilization in automated processes.

In accordance with the present invention the article to be positioned is held by a first carrier assembly which is supported shiftably on a second carrier. The second carrier is reciprocatively movable relative to the plane of said stations. As the second carrier is reciprocated the first carrier is shifted laterally by a cam and track guiding arrangement which serves to guide the work article positively into precise alignment with one and then the other station in an alternating sequence.

The cam and track arrangement comprises a pair of separated grooves (tracks) in a stationary pillar and a rotatable two-position cam supported on the pillar and forming discontinuous linking channels between said tracks. With each said reciprocation of the second carrier the cam guides a cam follower attached to the first carrier from one to the other said track, and in turn the cam is rotatably tipped by the motion of said follower is moving to the other track. This tipping prepares the cam to guide the follower back to the one track in a subsequent reciprocation. The tracks are in positional correspondence with respective said work stations so that upon completion of successive said reciprocations the work article is positioned precisely at first one and then the other of said stations.

The foregoing and other objects, features, aspects and advantages of the invention will be apparent from the following description of the preferred embodiment as illustrated in the accompanying drawings.

DESCRIPTION OF PREFERRED EMBODIMENT

Figure 1:
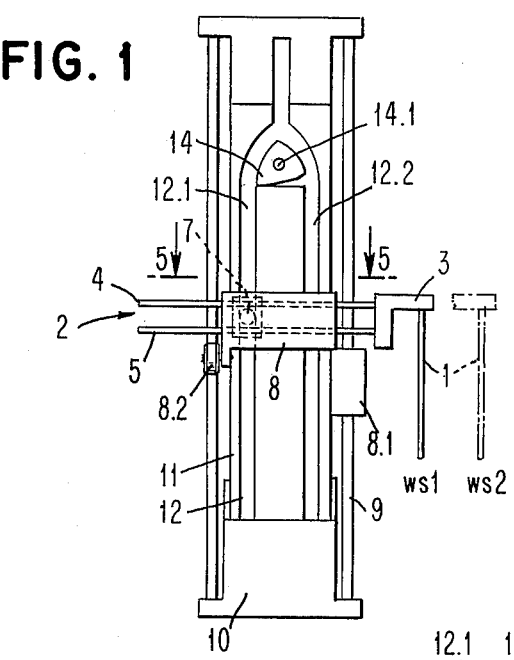
FIGS. 1 and 2 are front and rear elevational views of positioning apparatus in accordance with the present invention.
Figure 2:
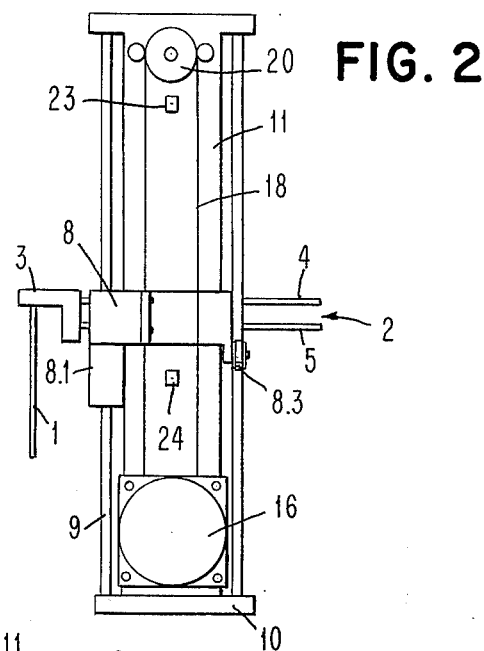
Figure 5:
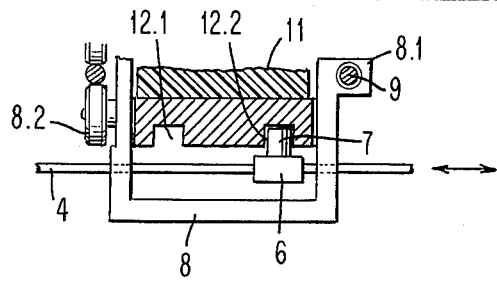
FIG. 5 is a top elevational view of a portion of the apparatus in FIG. 1 serving to illustrate the relationship between first and second carrier subassemblies of FIG. 1.

FIGS. 1, 2 and 5 provide respective front, rear and top (partial) elevational views of positioning apparatus in accordance with the present invention. The article 1 (in the illustration a test probe), which is to be positioned reciprocatively relative to the two work stations WS1, WS2, is retained on a first carrier subassembly 2. Subassembly 2 comprises holder 3, rods 4 and 5, follower base 6 and cam follower 7.

Follower 7 is attached to base 6 which in turn is fastened to rods 4 and 5. Holder 3 is also attached to the rods.

Rods 4 and 5 are supported slidably in vertical carrier 8 (FIGS. 1, 2, 5), the latter representing a portion of an elevator subassembly (hereafter "elevator"), which is movable vertically relative to the work stations. Member 8 has a sleeve-like part 8.1 which is keyed slidably over stationary rail 9, the latter supported on stationary base 10.

Pillar 11 supported on base 10 has a groove 12 (FIG. 1) which slidably receives cam follower 7. Cam 14 supported rotatably on pin 14.1, the latter fastened to pillar 11, forms a switching link between track sections 12.1 and 12.2 of groove 12. Sections 12.1 and 12.2 have positional correspondence with respective stations WS1 and WS2.

Base 10 supports an intermittently operated motor 16 (FIG. 2) linked to belt 18 (FIG. 2). Ends of belt 18 are fastened to carrier 8 (FIG. 2). The belt runs over pulley 20 (FIG. 2) which is rotatably supported on pillar 11.

A second rail 21 supported on base 10 forms an additional guide and support for member 8. A pair of rollers 8.2 (FIG. 1) and 8.3 (FIG. 2), attached to member 8, grip the rail 21 (front and rear) and roll along the rail. Rails 9 and 21 are secured rigidly by the top of pillar 11.

Figure 3:
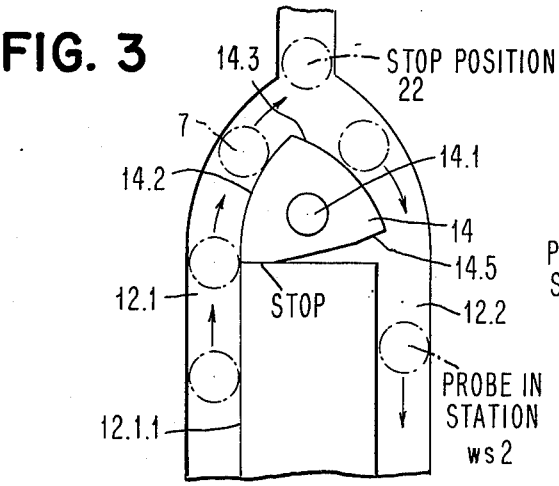
FIGS. 3 and 4 are views of the horizontal shifting subassembly of the apparatus of FIG. 1, illustrating the operation thereof.
Figure 4:
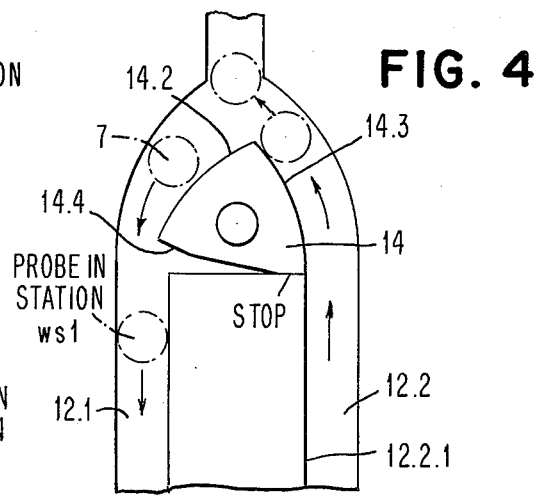
Figure 6:
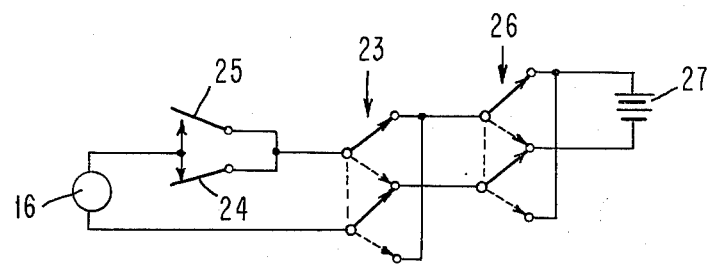
FIG. 6 is a schematic of electrical circuit controls suitable for controlling displacements of the vertical carrier 8 of FIG. 1.

In operation (refer to FIGS. 1-6) motor 16 is operated intermittently to transmit reciprocative vertical movement to carrier 8 (via belt 18). Carrier subassembly 2 follows this movement and shifts laterally due to the action of follower 7. Follower 7 rides upward in track 12.1 or 12.2 and as it reaches reversing limit postion 22 (FIG. 3) carrier 8 trips toggle microswitch 23 (FIGS. 2, 6) causing the motor 16 to reverse direction. As carrier 8 and follower 7 move downward cam 14 guides follower 7 into the opposite track 12.2 (if, as shown in FIG. 3, the upward movement was in 12.1) or 12.1 (if, as shown in FIG. 4, the upward movement was in 12.2). Consequently subassembly 2 is shifted laterally into registration with the opposite work station WS2 (if the upward movement originated with the probe in WS1, FIG. 3) or WS1 (if the upward movement originated with the probe in WS2, FIG. 4). In the downward movement cam 14 is tipped reversely (clockwise in FIG. 3, counter-clockwise in FIG. 4) in preparation for transferring follower 7 to the opposite track (12.1 FIG. 3; 12.2 FIG. 4) in the next cycle of upward and downward movement.

At the limit of downward movement (probe 1 in WS1 or WS2) carrier 8 operates normally closed microswitch 24 (FIGS. 2, 6) halting motor 16. A not-shown limit stop acts against carrier 8 to halt the elevator descent at a precise work position. A work operation may then be performed relative to probe 1 and at the conclusion of this operation switches 25 and 26 (FIG. 6) are operated, by not-shown work operation controls, to drive motor 16 in reverse (upward) direction, thereby re-mobilizing belt 18 and repeating the upward/downward reciprocation of carrier 8 and the lateral displacement of carrier subassembly 2. Switch 25 may be a normally open switch operated only momentarily to initiate the upward movement of the elevator and thereby release contact 24 to its normal closed position; and 26 may be a reversing toggle identical to 23 (see FIG. 6) for reversing polarity of drive excitation delivered from power source 27 to motor 16 (see FIG. 6).

The cam 14 serves three essential purposes: 1) Its camming surfaces 14.2 and 14.3 form partial continuations of respective surfaces 12.1.1 and 12.2.1 of respective tracks 12.1 and 12.2 when the cam is appropriately tipped (i.e., when respective surfaces 14.4 and 14.5 are positioned adjacent respective tracks as suggested in FIGS. 3 and 4 respectively). 2) The lengths of surfaces 14.2 and 14.3 are shorter than the displacements from respective tracks 12.1 and 12.2 to the reversing point 22, and consequently follower 7 invariably is deflected in its descent into the opposite track. 3) Finally, its lower surfaces 14.4 (FIG. 4) and 14.5 (FIG. 3) are arranged to cause the cam to be tipped at a precise reversing angle by the force exerted by follower 7 in its descent.

Obviously the cam should be initially orientated to form a partial surface continuation of the track (12.1 or 12.2) immediately containing cam follower 7; but if this is not true initially it will be true unavoidably after the first complete elevation reciprocation due to the form of the cam and the outer surfaces of the tracks.

Obviously by varying the form of carrier 8 to provide sufficient lateral clearance, and by providing additional reversely oriented U-shaped groove extensions of groove 12 and appropriate electrical switching controls, follower 7 may be made to shift laterally into other additional groove tracks to position object 1 relative to other additional work stations (besides WS1 and WS2).

While the invention has been particularly shown and described with reference to preferred embodiments thereof, it will be understood by those skilled in the art that various changes in form and detail may be made therein without departing from the spirit and scope of the invention.

What is claimed is:

1. Apparatus for positioning a work object precisely relative to first and second work stations in an alternating cyclic sequence, for execution of work operations at said stations, comprising:
   first and second carrier assemblies;
   said second assembly mounted for one-dimensional reciprocative movement relative to said stations;
   said first assembly carried by said second assembly and mounted to permit movement transverse to said one dimension;
   said first assembly including means for holding a said work object and a cam follower;
   stationary means having first and second cam tracks associated respectively with said first and second work stations, said cam follower being engageable with said tracks;
   a two-position rotatable cam carried on said stationary means and forming a linking channel between said first and second tracks for guiding said cam follower alternately from one to the other of said tracks when said second carrier is displaced relative to said stations; and
   means for reciprocatively displacing said second carrier relative to said stations for removing said object from one of said stations and for causing said cam to guide said object to the other of said stations.

2. Apparatus in accordance with claim 1 wherein said tracks and associated first and second surfaces of said cam form a partially discontinuous U-shaped channel such that in one position of said cam first surface forms a partial continuation of said first track and in another position of said cam said second surface forms a partial continuation of said second track.

3. Apparatus in accordance with claim 1 wherein said cam contains first and second discrete surfaces respectively associated with said first and second tracks and forming with said tracks a partially discontinuous U-shaped channel such that in one rotational position of said cam said first surface forms a partial continuation of said first track and in the other rotational position of said cam said second surface forms a partial continuation of said second track; said surfaces being characterized further in that the lengths thereof fall short of the apex of said U-shaped channel whereby said follower may be guided to the apex of said channel along one said surface before its direction of movement is reversed and invariably caused to engage the other said surface during its reverse movement; said cam being further characterized in that said engagement with said other surface in said reverse movement invariably causes rotation of said cam to position said other surface in continuing relationship to the respectively associated track.

4. Apparatus for positioning a work object precisely relative to plural work stations for execution of work operations at said stations comprising:
   a stationary guide assembly having first and second cam tracks associated with respective first and second said work stations;
   a movable carrier assembly mounted for movement relative to said tracks and having a cam follower engageable with said tracks; said carrier assembly serving to hold said work object;
   a variably displaceable, multifaceted cam rotatably mounted about an axis located within the facets of the said cam and situated at a junction between said tracks; said cam facets being contacted by and displaced by said cam follower in the course of movemet of said carrier assembly for transporting said object from one to the other of said respective work stations; said cam further being effective when displaced to operate to guide said follower from following engagement with a respective one of said tracks to the other of said tracks, thereby positioning said object at the respective other station.

5. Apparatus in accordance with claim 4 wherein said cam facets forms first and second surfaces for forming partial continuations of respective first and second said tracks; said cam having rotational clearance relative to ends of said tracks allowing rotational displacement of said cam into continuity relation with said tracks, said first and second surfaces serving alternately upon rotation to form partial continuations of the adjacent tracks, for guiding said follower out of one track and into another track.

* * * * *